United States Patent [19]
Coburn et al.

[11] Patent Number: 5,869,487
[45] Date of Patent: Feb. 9, 1999

[54] PYRIDO[3,4-B]PYRAZINES FOR USE AS THROMBIN INHIBITORS

[75] Inventors: Craig Coburn, Skippack; Christine Kolatac, St. Davids; Diane M. Rush, Perkasie; Joseph P. Vacca, Telford, all of Pa.

[73] Assignee: Merck & Co., Inc., Rahway, N.J.

[21] Appl. No.: 957,653

[22] Filed: Oct. 24, 1997

Related U.S. Application Data

[60] Provisional application No. 60/029,053 Oct. 24, 1996.
[51] Int. Cl.[6] .................. A61K 31/495; A61K 31/55; C07D 471/04
[52] U.S. Cl. .................. 514/249; 544/346; 544/350; 514/250; 514/220; 514/221; 540/501; 540/497
[58] Field of Search .................. 514/249; 544/350

[56] References Cited

U.S. PATENT DOCUMENTS

| | | | |
|---|---|---|---|
| 4,296,114 | 10/1981 | Appleton et al. | 424/248.52 |
| 5,260,307 | 11/1993 | Ackermann et al. | 514/323 |
| 5,272,158 | 12/1993 | Hartman et al. | 514/323 |
| 5,405,854 | 4/1995 | Ackermann et al. | 514/315 |
| 5,459,142 | 10/1995 | Tone et al. | 514/252 |
| 5,510,369 | 4/1996 | Lumma et al. | 514/422 |
| 5,602,253 | 2/1997 | Antonsson et al. | 544/330 |

FOREIGN PATENT DOCUMENTS

| | | |
|---|---|---|
| 0 262 096 | 3/1988 | European Pat. Off. |
| 0 509 769 A2 | 10/1992 | European Pat. Off. |
| 0 648 780 A1 | 4/1995 | European Pat. Off. |
| WO94/25051 | 11/1994 | WIPO. |
| 96/11697 | 4/1996 | WIPO. |
| 96/31504 | 10/1996 | WIPO. |
| 96/32110 | 10/1996 | WIPO. |
| 97/01338 | 1/1997 | WIPO. |

OTHER PUBLICATIONS

Mack et al., J. Enzyme Inhibition, "Design, Synthesis and Biological Activity of Novel Rigid Amidino–Phenylalanine Derivatives . . .", vol. 9, pp. 73–86 (1995).

Edwards et al., J. Am. Chem. Soc., "Design, Synthesis, and Kinetic Evaluation of a Unique Class of Elastase Inhibitors . . .", vol. 114, pp. 1854–1863 (1992).

Brown et al., J. Med. Chem., "Design of Orally Active, Non–Peptidic Inhibitors of Human Leukocyte Elastase", vol. 37, pp. 1259–1261 (1994).

Temple, Carroll, Jr. and Gregory A. Rener, J. Med. Chem., "Antimitotic Agents: Ring Analogues and Derivatives of Ethyl . . .", vol. 35, pp. 4809–4812 (1992).

Bernstein, et al., J. Med. Chem., 37, 3313–3326 "Nonpeptidic Inhibitors of Human Leukocyte Elastase . . .", 1994.

*Primary Examiner*—Mukund J. Shah
*Assistant Examiner*—Ann M. Kessinger
*Attorney, Agent, or Firm*—Richard S. Parr; Melvin Winokur

[57] ABSTRACT

A compound which inhibits human thrombin and where has the structure

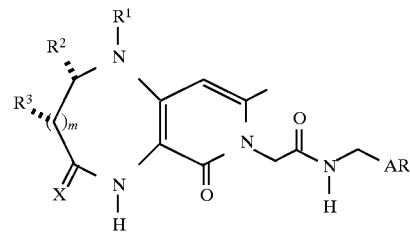

such as

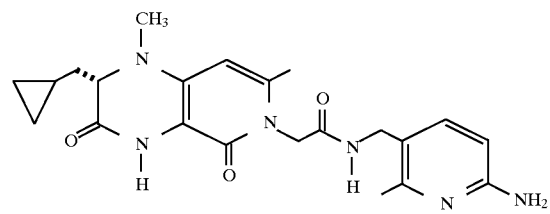

6 Claims, No Drawings

PYRIDO[3,4-B]PYRAZINES FOR USE AS THROMBIN INHIBITORS

CROSS-REFERENCE TO RELATED APPLICATIONS

This patent application is a non-provisional patent application claiming priority to U.S. provisional application 60/029,053, filed Oct. 24, 1996.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.* (1992) vol. 114, pp. 1854–63, describes peptidyl α-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoiminomethyl)amino]butyl]-1-[N-(2-naphthalenylsulfonyl)-L-phenylalanyl]-L-prolinamide.

WO 94/29336 describes compounds which are useful as thrombin inhibitors.

Compounds of the invention are bicyclic pyridone thrombin inhibitors. Dornow et al., *Chem. Ber.*, Vol. 99, pp. 244–253 (1966) describes a procedure for making bicyclic pyridones.

SUMMARY OF THE INVENTION

The invention relates to compounds of the formula:

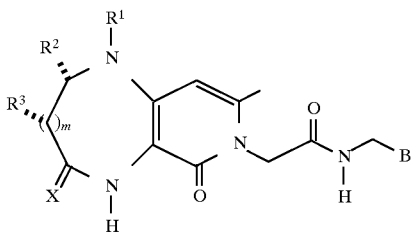

wherein
  m is 0 or 1;
  X is O or $H_2$;
  $R^1$, $R^2$ and $R^3$ are independently selected from the group consisting of
    hydrogen,
    $C_{1-6}$ alkyl-,
    $C_{2-6}$ alkenyl,
    $C_{2-6}$ alkynyl,
    $C_{3-8}$ cycloalkyl-,
    $C_{3-8}$cycloalkyl $C_{1-6}$alkyl-,
    aryl,
    aryl $C_{1-6}$ alkyl-,
      wherein aryl is phenyl either unsubstituted or substituted with —OH, —$NH_2$, $C_{1-6}$alkyl, $C_{3-8}$cycloalkyl, or halogen;
  or $R^1$ and $R^2$, along with the nitrogen atom to which $R^1$ is attached and the carbon atom to which $R^2$ is attached, form a five or six-membered saturated ring; and
  B is

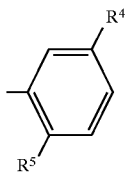

wherein $R^4$ and $R^5$ are independently selected from the group consisting of
    hydrogen,
    $C_{1-4}$ alkyl,
    $C_{2-4}$ alkenyl,
    $C_{2-4}$ alkynyl,
    $C_{1-4}$ alkoxy,
    halogen,
    —COOH,
    —OH,
    —COOR$^7$, where $R^7$ is $C_{1-4}$alkyl,
    —CONR$^8$R$^9$, where $R^8$ and $R^9$ are independently hydrogen or $C_{1-4}$alkyl,
    —OCH$_2$CO$_2$H,
    —OCH$_2$CO$_2$CH$_3$,
    —OCH$_2$CO$_2$(CH$_2$)$_{1-3}$CH$_3$,
    —O(CH$_2$)$_{1-3}$C(O)NR$^{10}$R$^{11}$, wherein $R^{10}$ and $R^{11}$ are independently hydrogen, $C_{1-4}$alkyl, $C_{3-7}$ cycloalkyl, or —CH$_2$CF$_3$,
    —(CH$_2$)$_{1-4}$OH,
    —NHC(O)CH$_3$,
    —NHC(O)CF$_3$,
    —NHSO$_2$CH$_3$,
    —SO$_2$NH$_2$;
  or B is

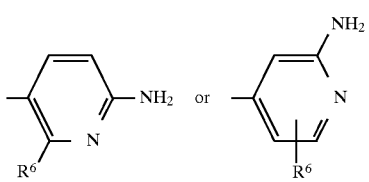

wherein $R^6$ is
    hydrogen,
    $C_{1-6}$ alkyl-,
    $C_{2-6}$ alkenyl-,
    $C_{2-6}$ alkynyl,
    $C_{3-8}$ cycloalkyl-,
    aryl,
    aryl $C_{1-6}$alkyl-, wherein aryl is phenyl either unsubstituted or substituted with —OH, —NH$_2$, C$_{1-6}$alkyl, C$_{3-8}$ cycloalkyl, or halogen.
and pharmaceutically acceptable salts thereof.

A class of these compounds is

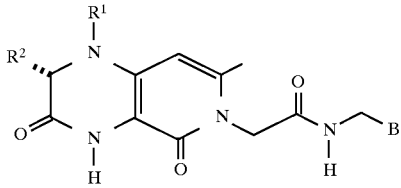

wherein

R$^1$ and R$^2$ are independently selected from the group consisting of:
hydrogen,
C$_{1-6}$alkyl,
C$_{3-8}$cycloalkylC$_{1-6}$alkyl-,
aryl C$_{1-6}$alkyl-,
wherein aryl is phenyl, or R$^1$ and R$^2$, along with the nitrogen atom to which R$^1$ is attached and the carbon atom to which R$^2$ is attached, form a five or six-membered saturated ring; and B is

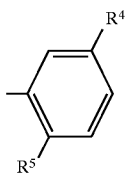

wherein R$^4$ and R$^5$ are independently selected from the group consisting of
hydrogen,
halogen,
—OCH$_2$C(O)NHR$^{11}$
or B is

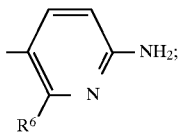

where R$^6$ is hydrogen or —CH$_3$,
and pharmaceutically acceptable salts thereof.

A group of this class of compounds is

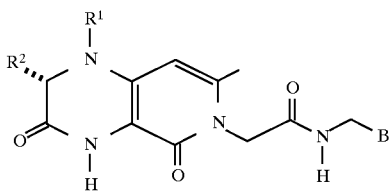

wherein

R$^1$ and R$^2$ are independently selected from the group consisting of:

hydrogen,
CH$_3$,

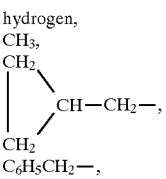

C$_6$H$_5$CH$_2$—, or R$^1$ and R$^2$, along with the nitrogen atom to which R$^1$ is attached and the carbon atom to which R$^2$ is attached, form a five or six-membered saturated ring; and B is

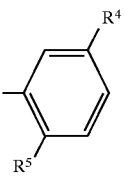

wherein R$^4$ and R$^5$ are independently selected from the group consisting of
hydrogen,
chloro,

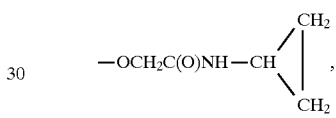

or B is

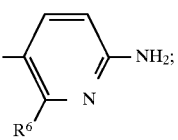

where R$^6$ is hydrogen or —CH$_3$,
and pharmaceutically acceptable salts thereof.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION

Compounds of the present invention, which are thrombin inhibitors, are useful in anticoagulant therapy. Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems The compounds of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinlypyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

For example, oral tablets can be prepared which contain an amount of active compound of between 100 and 500 mg, e.g. 100, 200, 300, 400 or 500 mg. Typically, a patient in need of thrombin inhibitor compound, depending on weight and metabolism of the patient, would be administered between about 100 and 1000 mg active compound per day. For a patient requiring 1000 mg per day, two tablets containing 250 mg of active compound can be administered in the morning and two tablets containing 250 mg of active compound can again be administered in the evening. For a patient requiring 500 mg per day, one tablet containing 250 mg of active compound can be administered in the morning and one tablet containing 250 mg of active compound can again be administered in the evening.

The compounds are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or betalactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds can also be co-administered with suitable anti-coagulation agents or thrombolytic agents such as plasminogen activators or streptokinase to achieve synergistic effects in the treatment of various ascular pathologies. For example, the compounds enhance the efficiency of tissue plasminogen activator-mediated thrombolytic reperfusion.

The compounds may be administered first following thrombus formation, and tissue plasminogen activator or other plasminogen activator is administered thereafter. They may also be combined with heparin, aspirin, or warfarin.

Specific embodiments of compounds of the invention are shown in the table below. These compounds inhibit thrombin with the following potency according to in vitro measurements:

| Structure | thrombin Ki (nM) <br> * > 1.0 <br> ** < 1.0 |
| --- | --- |
|  | ** |
|  | ** |
|  | ** |
|  | * |
|  | * |

| Structure | thrombin Ki (nM)<br>* > 1.0<br>** < 1.0 |
|---|---|
| [Structure with cyclopropyl, CH3-N, pyrazinone, glycinamide, methylpyridine-NH2] | ** |
| [Structure with cyclopropyl, CH3-N, pyrazinone, glycinamide, pyridine-NH2] | ** |
| [Structure with cyclopropyl, CH3-N, pyrazinone, glycinamide, phenoxy-acetyl-cyclopropylamine] | ** | and pharmaceutically acceptable salts thereof.

In vitro assay for determining proteinase inhibition

Assays of human α-thrombin and human trypsin were performed at 25° C. in 0.05M TRIS buffer pH 7.4, 0.15M NaCl, 0.1% PEG. Trypsin assays also contained 1 mM $CaCl_2$.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human α-thrombin ($K_m=125$ μM) and human trypsin ($K_m=59$ μM). p-Nitroanilide substrate concentration was determined from measurements of absorbance at 342 nm using an extinction coefficient of 8270 $cm^{-1}M^{-1}$.

In certain studies with potent inhibitors ($K_i<10$ nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) ($K_m=27$ μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration 0.5 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Some abbreviations that may appear in this application are as follows.
Designation
BOC (Boc) t-butyloxycarbonyl
HBT(HOBT or HOBt) 1-hydroxybenzotriazole hydrate
BBC reagent benzotriazolyloxy-bis(pyrrolidino)-carbonium hexafluorophosphate
PyCIU 1,1,3,3-bis(tetramethylene)-chlorouronium hexafluorophosphate
EDC 1-ethyl-3-(3-dimethylaminopropyl)carbodiimide hydrochloride (BOC)₂O di-t-butyl dicarbonate
DMF dimethylformamide
Et₃N or TEA triethylamine
EtOAc ethyl acetate
TFA trifluoroacetic acid
DMAP dimethylaminopyridine
DME dimethoxyethane
BH₃-THF Borane-tetrahydrofuran complex
D-Phe(3,4-Cl₂) D-3,4-Dichlorophenylalanine
D-3,3-dicha D-3,3-Dicyclohexylalanine
Pro Proline
Arg Arginine
Gly Glycine
D-3,3,-diphe D-3,3-Diphenylalanine
LAH lithium aluminum hydroxide
Cy cyclohexyl
POCl₃ phosphorous oxychloride
MeCN acetonitrile
BnEt₃N⁺Cl⁻ benzyl triethyl ammonium chloride
NaH sodium hydride
DMF dimethylformamide
BrCH₂COO'Bu tert butyl bromoacetate
EtOH ethyl alcohol
Pd(C) palladium on activated carbon catalyst
CF₃COOH trifluoroacetic acid
DCM dichloromethane
DIPEA diisopropylethylamine The compounds of the present invention may have chiral centers and occur as racemates, racemic mixtures and as individual diastereomers, or enantiomers with all isomeric forms being included in the present invention.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like. The term "alkenyl" means straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like. The term "alkynyl" means straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like. Cycloalkyl means a cyclic, saturated ring containing 3 to 8 carbon atoms, e.g., cyclopropyl, cyclohexyl, etc. Halogen means chloro, bromo, fluoro or iodo.

The pharmaceutically-acceptable salts of the compounds of the invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

Compounds of the invention can be prepared according to the following general synthetic strategy:

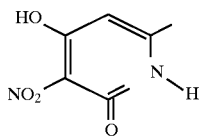

is chlorinated with, for example, phosphorous oxychloride, acetonitrile and benzyltriethylammonium chloride, to form

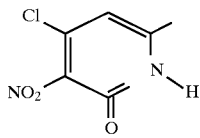                                                                    I

I is then alkylated with for example, sodium hydride, dimethyl formamide and tert-butyl bromoacetate, to form

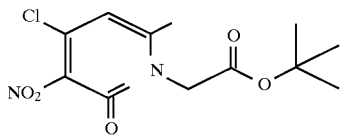                                                                    II II is subjected to Michael addition with

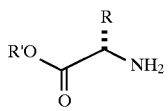

using, for example, ethyl alcohol under heated conditions, to form

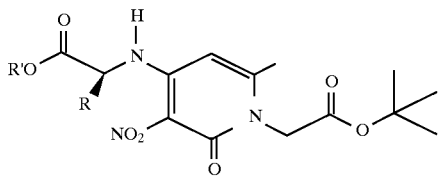                                                                    III Reductive ring closure of III using, for example, hydrogen gas and palladium on activated carbon catalyst, forms

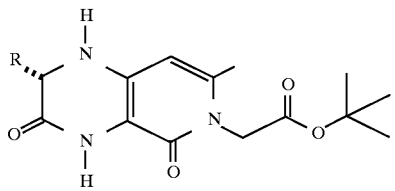                                                                    IV Hydrolysis of IV with, for example, trifluoracetic acid and dicloromethane at around 0° C., forms

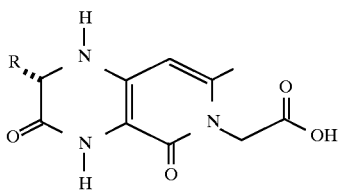

Amide coupling of V with

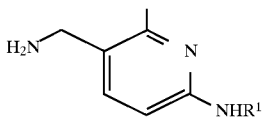

(Where R¹ is hydrogen or a BOC protecting group) using, for example, ethylene dichloride, 1-hydroxybenzotriazole hydrate, and diisopropylethylamine, forms

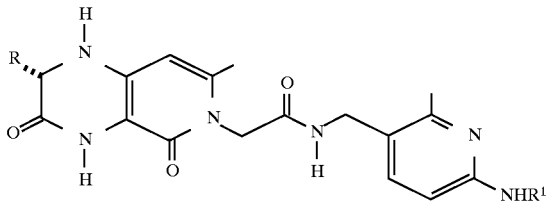

Where R¹ is hydrogen, VI represents the finished product. Where R¹ is BOC, VI is deprotected with hydrogen chloride and ethyl acetate to form the finished product.

Unless otherwise stated, all NMR determinations were made using 400 MHz field strength.

Intermediates used to prepare compounds of the invention were prepared as follows:

Preparation of L-Cyclopropylalanine Methyl Ester Hydrochloride

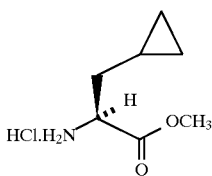

Step 1

N-Boc-L-2-amino-4-pentenoic acid

To a solution of L-2-amino-4-pentenoic acid (1.15 g, 10.0 mmol) in a mixture of dioxane (10 mL) and 1N NaOH (10 mL) was stirred in an ice bath. Di-tert-butyl pyrocarbonate (2.4 g, 11.0 mmol) was added and stirring was continued for 1 h. The solution was concentrated to 10 mL and 30 mL of EtOAc was added. The solution was made acidic (pH=3) by the addition of solid KHSO$_4$. The aqueous phase was extracted with EtOAc (2×10 mL) and dried over MgSO$_4$. Evaporation of the solvent afforded the N-Boc protected amino acid as a white solid.

$^1$H NMR (CDCl$_3$) δ 5.75 (m, 1H), 5.20 (m, 2H), 5.05 (d, J=5.0 Hz, 1H), 4.40 (d, J=5.0 Hz, 1H), 4.57 (m, 2H), 1.47 (s, 9H).

Step 2

N-Boc-L-cyclopropylalanine Methyl Ester

To a solution of N-Boc-L-2-amino-4-pentenoic acid (2.15 g, 10.0 mmol) in 50 mL of ether was added 100 mL of ethereal diazomethane (0.5M, 50 mmol) by pipet. After the addition was complete, 225 mg (1.0 mmol) of Pd(OAc)$_2$ was added cautiously causing the vigorous release of N$_2$. Stirring was continued for 2 h. The solution was purged with argon gas, filtered through Celite and concentrated. The residue was chromatographed (1:9 EtOAc/Hexanes) to afford 2.41 g (100%) of the cyclopropanated amino ester.

$^1$H NMR (CDCl$_3$) δ 5.20 (bs, 1H), 4.43 (d, J=5.0 Hz, 1H), 3.78 (s, 3H), 1.63 (m, 2H), 1.47 (s, 9H), 0.72 (m, 1H), 0.48 (m, 2H), 0.07 (m, 2H).

Step 3

L-Cyclopropylalanine Methyl Ester

HCl gas was bubbled through a 0° C. solution of N-Boc-L-Cyclopropylalanine methyl ester (2.41 g, 10.0 mmol) in 10 mL of EtOAc for 5 min. The solvent was removed in vacuo and the resulting solid was triturated with ether to afford the title compound.

$^1$H NMR (CD$_3$OD) δ 4.10 (t, J=7.4 Hz, 1H), 3.83 (s, 3H), 1.93 (m, 1H), 1.77 (m, 1H), 0.79 (m, 1H), 0.58 (m, 2H), 0.11 (m, 2H).

Preparation of N-Methyl-L-Cyclopropylalanine Methyl Ester Hydrochloride

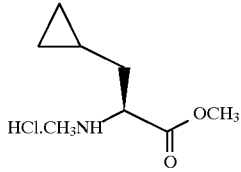

Step 1

N-Boc-N-methyl-L-Cyclopropylalanine Methyl Ester

A solution of 3.5 g (14.5 mmol) of N-Boc-L-Cyclopropylalanine methyl ester from step 2 above was dissolved in 10 mL of DMF and treated with 10 mL (161.5 mmol) of methyl iodide followed by 7.0 g (30.2 mmol) of Ag$_2$O and the resulting mixture was heated at 55° C. for 24 h. The reaction mixture was cooled, diluted with 20 mL of ether and filtered through a pad of Celite. The filtrate was washed with water (7×5 mL) and dried over MgSO$_4$. Evaporation of the solvent afforded 2.7 g (73%) of the title compound which was used directly in the next step without further purification.

$^1$H NMR (CDCl$_3$, 1:1 mixture of rotomers) δ 4.80 (bs, 0.5H), 4.40 (bs 0.5H), 3.75 (s, 3H), 2.85 (s, 1.5H), 2.80 (s, 1.5H), 1.90–1.6 (m, 2H), 1.47 (s, 4.5H), 1.45 (s, 4.5H), 0.68 (m, 1H), 0.43 (m, 2H), 0.05 (m, 2H).

Step 2

N-Methyl-L-Cyclopropylalanine Methyl Ester

HCl gas was bubbled through a 0° C. solution of N-Boc-N-Methyl-L-cyclopropylalanine methyl ester (2.7 g, 10.7 mmol) in 10 mL of EtOAc fo 5 min. The solvent was removed in vacuo and the resulting solid was triturated with ether to afford the title compound.

$^1$H NMR (CDCl$_3$) δ 9.80 (bs, 1H), 3.90 (s, 4H), 2.80 (s, 3H), 2.04 (m, 2H), 0.95 (m, 1H), 0.58 (m, 2H), 0.18 (m, 2H).

EXAMPLE 1

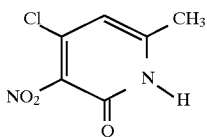

To a solution of 4-hydroxy-6-methyl-3-nitropyridone (Fluka, 3.15 g, 18.5 mmol) and 16.8 g (74 mmol) of BnEt$_3$NCl in 65 mL of MeCN was added 7.6 mL (81.4 mmol) of POCl$_3$. The resulting solution was stirred at 40° C. for 30 min then heated at reflux for 1 h. After evaporation of the solvent, 70 mL of water was added and the mixture was stirred at room temperature for 16 h. The precipitate which formed was filtered and washed with hexane to afford 1-1 as a yellow solid.

$^1$H NMR (DMSO-d$_6$) δ 6.45 (s, 1H), 2.25 (s, 3H).

HPLC R$_f$=0.43.

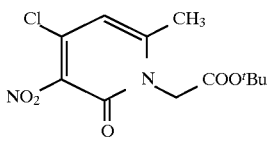

To a 0° C. solution of 4-chloro-6-methyl-3-nitropyridone 1-1 (3.93 g, 20.8 mmol) in 80 mL of DMF was added 550 mg (22.9 mmol) of NaH. The resulting solution was stirred at 0° C. for 15 min then treated with 3.69 mL (25.0 mmol) of tert-butyl bromo acetate. The homogeneous solution was allowed to stir to room temperature over 16 h. After evaporation of the solvent, the residue was partitioned between EtOAc and water. The organic phase was washed with brine, dried (MgSO$_4$) and concentrated. Column chromatography (1:1 EtOAc/Hexanes) of the dark brown oil gave 1-2 as a light brown solid.

$^1$H NMR (CDCl$_3$) δ 6.21 (s, 1H), 4.75 (s, 2H), 2.35 (s, 3H), 1.45 (s, 9H).

HPLC Rf=0.71

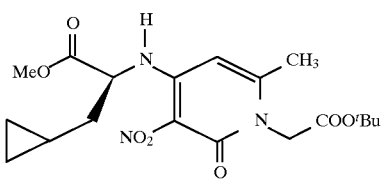

To a solution of pyridone 1-2 (401 mg, 1.32 mmol) in 6 mL of EtOH was added 239 mg (1.32 mmol) of L-cyclopropylalanine methyl ester hydrochloride was added 0.46 mL (3.3 mmol) of Et$_3$N. The solution was stirred at 70° C. for 15 h, cooled and evaporated to an oil. The residue was partitioned between EtOAc and water and the organic phase was washed with brine, dried (MgSO$_4$) and concentrated. Column chromatography (3:7 EtOAc/Hexanes) provided amine 1-3 as a white solid.

$^1$H NMR (CDCl$_3$) δ 9.62 (d, J=7.3 Hz, 1H), 5.61 (s, 1H), 4.72 (d, J=17.4 Hz, 1H), 4.55 (d, J=17.4 Hz, 1H), 4.33 (q, J=6.6 Hz, 1H), 3.80 (s, 3H), 2.27 (s, 3H), 1.95 (m, 1H), 1.92 (m, 1H), 1.47 (s, 9H), 0.76 (m, 2H), 0.58 (m, 2H), 0.17 (m, 2H).

HPLC R$_f$=0.69.

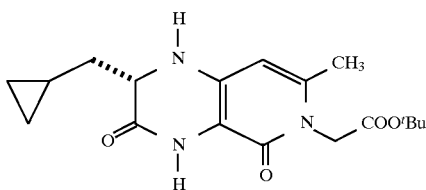

A solution of nitro ester 1-3 (479 mg, 1.17 mmol) and 48 mg of palladium on charcoal (10%) in 20 mL of EtOAc was hydrogenated over 30 h. The solution was filtered through Celite (EtOAc washes) and concentrated. The residue was subjected to column chromatography (2:3 EtOAc/Hexanes) to afford amine 1-4 as a white solid.

$^1$H NMR (CDCl$_3$) δ 7.76 (s, 1H), 5.70 (s, 1H), 4.88 (s, 1H), 4.70 (q, J=7.4 Hz, 2H), 4.33 (m, 2H), 2.19 (s, 3H), 1.81 (m, 1H), 1.63 (m, 1H), 1.47 (s, 9H), 0.78 (m, 1H), 0.58 (m, 1H), 0.45 (m, 1H), 0.11 (m, 1H), 0.07 (m, 1H).

HPLC Rf=0.58.

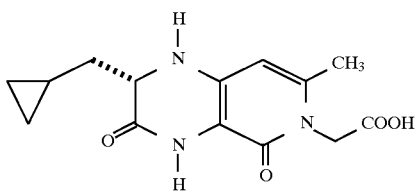

A 0° C. solution of ester 1-4 (201 mg, 0.576 mmol) in 7 mL of DCM treated with 5 mL of CF$_3$COOH. The cold solution was stirred for 1 h and concentrated to a dark oil. The residue was azeotroped with benzene (3×10 mL), EtOAc (2×10 mL) then ether (1×10 mL). The obtained oil was stirred with 5% MeOH in Et$_2$O to yield acid 1-5 as a tan solid.

$^1$H NMR (CD$_3$OD) δ 5.93 (s, 1H), 4.79 (s, 2H), 4.13 (m, 1H), 2.25 (s, 3H), 1.75 (m, 1H), 1.63 (m, 1H), 0.78 (m, 1H), 0.43 (m, 2H), 0.12 (m, 2H).

HPLC R$_f$=0.41.

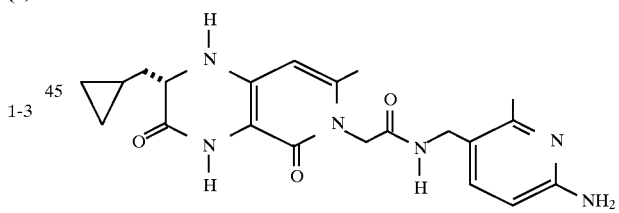

To a solution of carboxylic acid 1-5 (85 mg, 0.292 mmol) and 2-amino-5-aminomethyl-6-methylpyridine (120 mg, 0.876 mmol) in 2 mL of DMF was added 168 mg (0.876 mmol) of EDCI and 118 mg (0.876 mmol) of HOBT followed by 0.25 mL (1.46 mmol) of DIPEA. The homogeneous mixture was stirred at room temperature for 16 h after which time the solvent was removed under reduced pressure. The residue was subjected to column chromatography (1:9 CH$_3$OH/CHCl$_3$ sat'd with NH$_3$) to afford compound 1-6 as a white solid.

$^1$H NMR (CD$_3$OD) δ 7.36 (d, J=8.4 Hz, 1H), 6.39 (d, J=8.4 Hz, 1H), 5.90 (s, 1H), 4.71 (s, 2H), 4.26 (s, 2H), 4.11 (m, 1H), 2.34 (s,3H), 2.24 (s, 3H), 1.71 (m, 1H), 1.63 (m, 1H), 0.81 (m, 1H), 0.43 (m, 2H), 0.12 (m, 2H).

HPLC R$_f$=0.42.

Anal. Calc'd for C$_{21}$H$_{26}$N$_6$O$_3$0.65 CH$_2$Cl$_2$:C; 55.83, H; 5.91, N; 18.05. Found: C; 55.85, H; 6.04, N; 17.99.

EXAMPLE 2

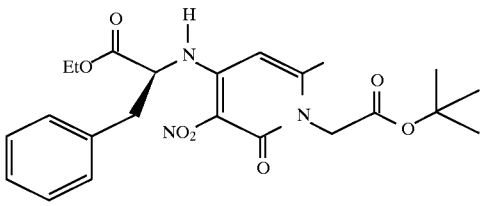

To a solution of pyridone 1-2 (300 mg, 0.990 mmol) in 20 mL of EtOH was added 318 mg (1.38 mmol) of L-phenylalanine ethyl ester hydrochloride. To this was added 0.344 mL (2.47 mmol) of Et$_3$N. The solution was stirred at 70° C. for 15 h, cooled and evaporated to a foam. The residue was partitioned between EtOAc and water. The organic phase was washed with brine, dried (MgSO$_4$) and concentrated. Column chromatography (95:5:1 CH$_2$Cl$_2$/CH$_3$OH/NH$_4$OH) provided amine 2-1 as a tan foam.

$^1$H NMR (CDCl$_3$) δ 9.62 (d, J=7.3 Hz, 1H), 7.23 (m, 5H), 5.61 (s, 1H), 4.58 (q, J=17.3 Hz, 2H), 4.47 (m, 1H), 4.12 (m, 2H), 3.23 (m, 2H), 2.18 (s, 3H), 1.45 (s, 9H), 1.23 (t, J=7.14 Hz, 3H).

HPLC R$_f$=0.74.

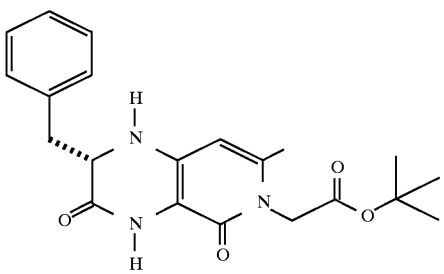

A solution of nitro ester 2-1 (440 mg, 0.957 mmol) and 88 mg of palladium on charcoal (10%) in 40 mL of THF was hydrogenated over 12 h. The solution was filtered through Celite (THF washes) and concentrated. The residue was subjected to column chromatography (95:5:1 CH$_2$Cl$_2$/CH$_3$OH/NH$_4$OH) to afford amine 2-2 as a yellow solid.

$^1$H NMR (CDCl$_3$) δ 7.85 (s, 1H), 7.23 (m, 5H), 5.58 (s, 1H), 5.23 (s, 3H), 4.63 (m, 2H), 4.29 (m, 1H), 4.15 (m, 2H), 3.23 (m, 1H), 2.80 (m, 1H), 2.17 (s, 3H), 1.43 (s, 9H).

HPLC Rf=0.62.

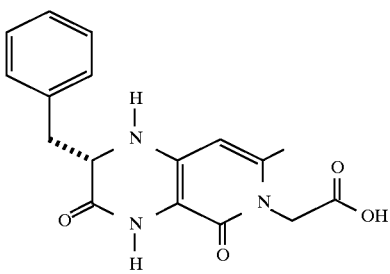

A 0° C. solution of ester 2-2 381 mg (1.0 mmol) in 15 mL of DCM treated with 5 mL of CF$_3$COOH. The cold solution was stirred for 5 h and concentrated to a dark oil. The residue was azeotroped with benzene (3×10 mL), EtOAc (2×10 mL) then ether (1×10 mL). The obtained oil was stirred with 5% MeOH in Et$_2$O to yield acid 2-3 as a brown foam.

$^1$H NMR (CD$_3$OD) δ 7.22 (m, 5H), 5.93 (s, 1H), 4.79 (m, 2H), 4.13 (m, 2H), 3.12 (m, 1H), 2.20 (s, 3H).

HPLC R$_f$=0.46.

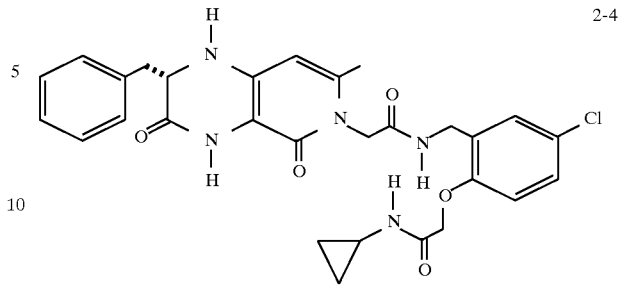

To a solution of carboxylic acid 2-3 (56 mg, 0.164 mmol) and N-cyclopropyl (2-aminomethyl-5-chlorophenoxy) acetamide (71 mg, 0.164 mmol) in 5 mL of DMF was added 47 mg (0.247) of EDCI and 33 mg (0.247 mmol) of HOBT followed by 0.08 mL (0.574 mmol) of Et$_3$N. The homogeneous mixture was stirred at room temperature for 16 h after which time the solvent was removed under reduced pressure. The residue was subjected to column chromatography (95:5:0.5 CH$_2$Cl$_2$/CH$_3$OH/NH$_4$OH) to afford compound 2-4 as a tan solid.

$^1$H NMR (CDCl$_3$) δ 9.80 (bs, 1H), 8.25 (bs, 1H), 7.75 (bs, 1H), 7.37 (d, J=2.4 Hz, 1H), 7.25 (m, 5H), 7.00 (dd, J=2.4 and 8.4 Hz, 1H), 6.58 (d, J=8.4 Hz, 1H), 5.55 (s, 1H), 4.65–4.40 (m, 6H), 3.35 (d, J=1H), 2.81 (m, 1H), 2.60 (m, 1H), 2.40 (s,3H), 0.9 (m, 3H), 0.65 (M, 2H).

HPLC R$_f$=0.63.

EXAMPLE 3

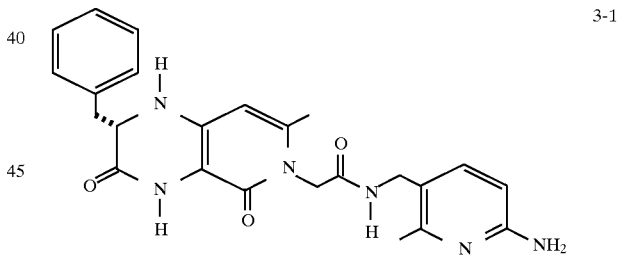

To a solution of carboxylic acid 2-3 (97 mg, 0.298 mmol) and 2-amino-5-aminomethyl-6-methylpyridine (45 mg, 0.328 mmol) in 10 mL of DMF was added 79 mg (0.417) of EDCI and 56 mg (0.417 mmol) of HOBT followed by 0.20 mL (1.19 mmol) of DIPEA. The homogeneous mixture was stirred at room temperature for 16 h after which time the solvent was removed under reduced pressure. The residue was subjected to column chromatography (90:10:1 C$_2$Cl$_2$/CH$_3$OH/NH$_4$OH) to afford compound 3-1 as a tan oil. HCl/ether was added to form the solid dihydrochloride salt.

$^1$H NMR (CD$_3$OD) δ 7.57 (d, J=8.4 Hz, 1H), 7.21 (m, 5H), 6.58 (d, J=8.4 Hz, 1H), 5.86 (s, 1H), 4.65 (m, 2H), 4.26 (s, 2H), 3.81 (m, 2H), 2.40 (s,3H), 2.20 (s, 3H).

HPLC R$_f$=0.45.

EXAMPLE 4

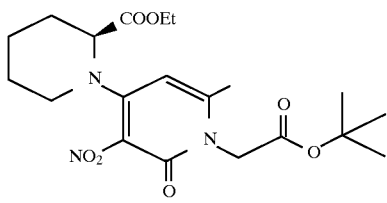
4-1

To a solution of pyridone 1-2 (800 mg, 2.64 mmol) in 25 mL of absolute ethanol was added L-homoproline ethyl ester (416 mg, 2.64 mmol), followed by 0.48 mL of triethylamine. The resulting solution was refluxed for 4.5 hours, then cooled to room temperature. After evaporation of the ethanol, the residue was partitioned between ethyl acetate and water. The organic phase was washed with brine, dried (MgSO$_4$), and concentrated to afford 4-1 as a dark yellow solid.

$^1$H NMR (CDCl$_3$) δ 5.78 (s, 1H), 4.66 (q, J=17.4 Hz, 2H), 4.22 (q, J=7.05 Hz, 2H), 3.34 (m, 2H), 2.25 (s, 3H), 2.22 (m, 1H), 1.85 (m, 1H), 1.76 (m, 1H), 1.65 (m, 2H), 1.55 (m, 2H), 1.48 (s, 9H), 1.29 (t, J=7.14 Hz, 3H).

HPLC R$_f$=0.71

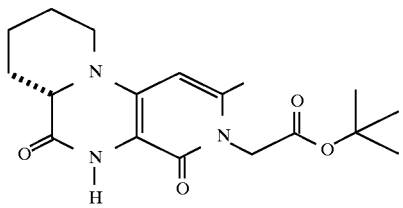
4-2

A solution of nitro ester 4-1 (1.10 g, 2.60 mmol) and 500 mg of palladium on carbon (10%) in 20 mL of EtOAc was hydrogenated at STP over 17 hours. The solution was filtered through Celite, washed with EtOAc, and concentrated to afford amine 4-2 as a solid.

$^1$H NMR (CDCl$_3$) δ 7.78 (s, 1H), 5.84 (s, 1H), 4.73 (s, 2H), 3.80 (t, J=15.0 Hz, 2H), 2.86 (t, J=12.3 Hz, 2H), 2.25 (s, 3H), 2.19 (m, 1H), 2.00 (m, 1H), 1.70 (m, 1H), 1.58 (m, 3H), 1.49 (s, 9H).

HPLC R$_f$=0.61

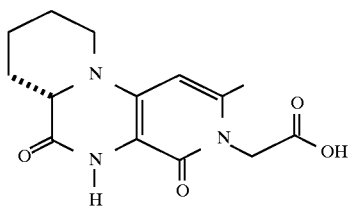
4-3

A solution of ester 4-2 (700 mg, 2.02 mmol) in 3 mL of DCM at 0° C. was treated with 3 mL of CF$_3$COOH. After stirring for 2 hours at RT, the solution was concentrated to an oil. The residue was azeotroped with toluene (6×20 mL) to afford acid 4-3 as a tan solid.

$^1$H NMR (CDCl$_3$) δ 8.05 (s, 1H), 5.94 (s, 1H), 4.78 (s, 2H), 3.86 (d, J=13.55 Hz, 2H), 2.89 (t, J=12.6 Hz, 1H), 2.70 (m, 1H), 2.36 (s, 3H), 2.20 (m, 1H), 2.01 (m, 1H), 1.73 (m, 1H), 1.60 (m, 3H).

HPLC R$_f$=0.45

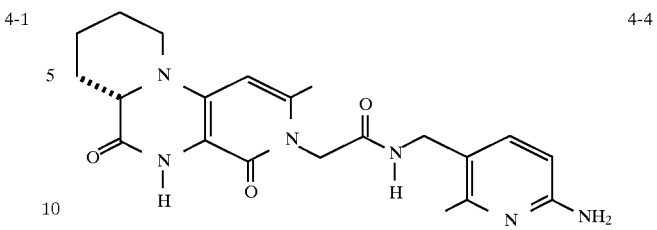
4-4

To a solution of acid 4-3 (300 mg, 1.03 mmol) and 2-BOC-amino-5-aminomethyl-6-methylpyridine (700 mg, 3.10 mmol) in 10 mL of DMF was added HOBT (419 mg, 3.10 mmol), EDC (595 mg, 3.10 mmol), and N,N-diisopropylethyl amine (0.54 mL, 3.10 mmol). The resulting solution was stirred overnight and concentrated. The residue was redissolved in EtOAc and washed with 5% Na$_2$CO$_3$, water, and brine. The organic phase was dried (MgSO$_4$) and concentrated to a solid. Purification of the solid by column chromatography (8% MeOH/EtOAc), yielded 270 mg (53%) of solid. From that product 100 mg was dissolved in EtOAc at 0° C. and subjected to HCl(g) for 10 min then stirred for 1 hour. The solution was concentrated to afford the final product 4-4 as a dark yellow solid.

$^1$H NMR (CD$_3$OD) δ 7.87 (d, J=8.97 Hz, 1H), 6.82 (d, J=9.15 Hz, 1H), 6.22 (s, 1H), 4.74 (s, 2H), 4.30 (s, 2H), 3.40 (m, 1H), 3.87 (m, 1H), 2.93 (t, J=12.91 Hz, 1H), 2.51 (s, 3H), 2.32 (s, 3H), 2.03 (m, 2H), 1.61 (m, 4H).

HPLC R$_f$=0.38

EXAMPLE 5

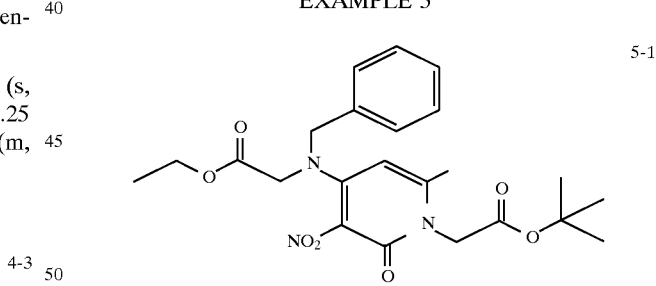
5-1

To a solution of pyridone 1-2 (500 mg, 1.65 mmol) in 15 mL of absolute ethanol was added N-benzyl glycine ethyl ester (320 mg, 1.65 mmol), followed by 0.30 mL of triethylamine. The resulting solution was refluxed for overnight, then cooled to room temperature. After evaporation of the ethanol in vacuo, the residue was partitioned between ethyl acetate and water. The organic phase was washed with brine, dried (MgSO$_4$), and chromatographed (2:3 EtOAc/Hexane) to afford 5-1 as a yellow solid.

$^1$H NMR (CDCl$_3$) δ 7.32 (m, 5H), 5.81 (s, 1H), 4.65 (s, 2H), 4.62 (s, 2H), 4.16 (q, J=7.05 Hz, 2H), 3.87 (s, 2H), 2.20 (s, 3H), 1.47 (s, 9H), 1.25 (t, 3H).

HPLC $R_f$=0.73

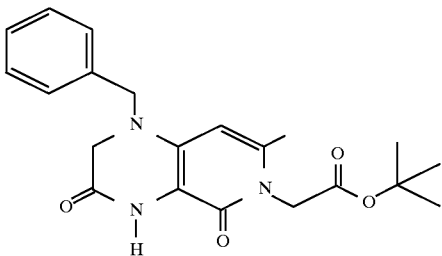
5-2

A solution of nitro ester 5-1 (185 mg, 0.403 mmol) and 100 mg of palladium on carbon (10%) in 10 mL of EtOAc was hydrogenated at STP over 17 hours. The solution was filtered through Celite, washed with EtOAc, and concentrated to afford amine 5-2 as a solid.

$^1$H NMR (CDCl$_3$) δ 7.91 (s, 1H), 7.33 (m, 5H), 5.84 (s, 1H), 4.72(s, 2H), 4.46 (s, 2H), 3.91 (s, 2H), 2.20 (s, 3H), 1.49 (s, 9H).

HPLC $R_f$=0.65

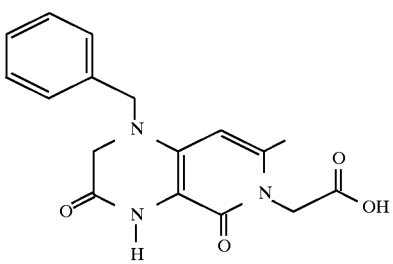
5-3

A solution of ester 5-2 (110 mg, 0.287 mmol) in 3 mL of DCM at 0° C. was treated with 3 mL of CF$_3$COOH. The ice bath was removed and stirring was continued for 2 hours. The solution was concentrated to an oil and the resulting residue was azeotroped with toluene (6×20 mL) to afford acid 5-3 as a yellow solid.

$^1$H NMR (CD$_3$OD) δ 7.31 (m, 5H), 6.21 (s, 1H), 4.83 (s, 2H), 4.59(s, 2H), 3.92(s, 2H), 2.79 (s, 3H).

HPLC $R_f$=0.51

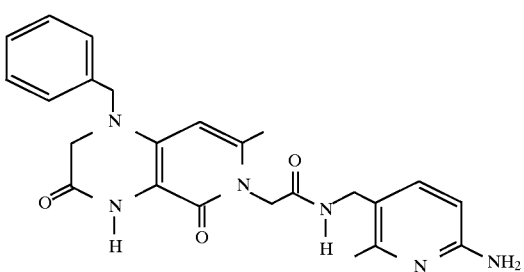
5-4

To a solution of acid 5-3 (99.7 mg, 0.305 mmol) and 2-amino-5-aminomethyl-6-methylpyridine (6.04 mg, 0.305 mmol) in 2 mL of DMF was added HOBT (41.0 mg, 0.305 mmol), EDC (59.0 mg, 0.305 mmol), and DIPEA (106 mL, 0.609 mmol). After stirring the resulting solution overnight, it was concentrated to an oil. The crude oil was purified by crystallization with EtOAc and methanol to yield 5-4 as a light yellow solid.

$^1$H NMR (CD$_3$OD) δ 7.86 (d, J=9.16 Hz, 1H), 7.32 (m, 5H), 6.81 (d, J=9.15 Hz, 1H), 6.36 (s, 1H), 5.39 (s, 2H), 4.80 (s, 2H), 4.29 (s, 2H), 2.50 (s, 3H), 2.31 (s, 3H).

HPLC $R_f$=0.48

EXAMPLE 6

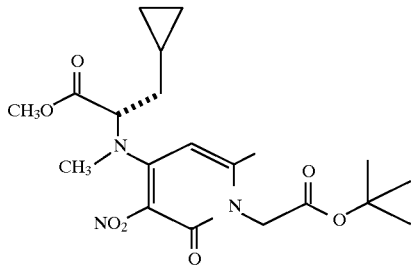
6-1

To a solution of pyridone 1-2 (1.00 g, 3.30 mmol) in 30 mL of absolute ethanol was added N-methyl-L-cyclopropylalanine methyl ester hydrochloride (639 mg, 3.30 mmol), followed by 1.15 mL of triethylamine. The resulting solution was refluxed for overnight, then cooled to room temperature. After evaporation of the ethanol in vacuo, the residue was partitioned between ethyl acetate and water. The organic phase was washed with brine, dried (MgSO$_4$) to afford 6-1 as a yellow solid.

$^1$H NMR (CDCl$_3$) δ 5.83 (s, 1H), 4.67 (s, 2H), 4.33 (m, 1H), 3.78 (s, 3H), 2.88 (s, 3H), 2.27 (s, 3H), 2.13 (m, 1H), 1.48 (s, 9H), 1.28 (m, 1H), 0.79 (m, 1H), 0.53 (m, 2H), 0.15 (m, 2H).

HPLC $R_f$=0.76

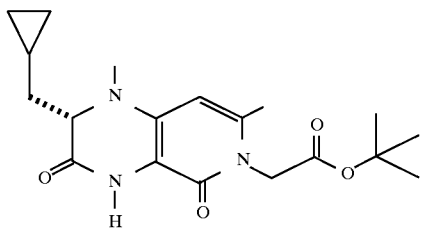
6-2

A solution of nitro ester 6-1 (1.50 g, 3.54 mmol) and 800 mg of palladium on carbon (10%) in 30 mL of EtOAc was hydrogenated over 48 hours. The solution was filtered through Celite, washed with EtOAc, and concentrated to afford amine 6-2 as a solid.

$^1$H NMR (CDCl$_3$) δ 7.82 (s, 1H), 5.76 (s, 1H), 4.73(q, J=17.58 Hz, 2H), 3.99 (t, J=5.31 Hz, 1H), 3.01 (s, 3H), 2.25 (s, 3H), 1.67(m, 2H), 1.48 (s, 9H), 0.65 (m,1H), 0.42 (m, 2H), 0.052 (m, 2H).

HPLC $R_f$=0.65

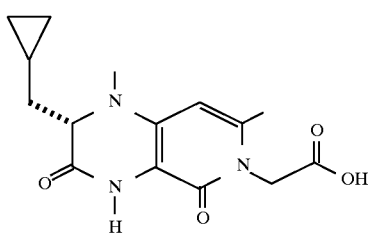
6-3

A solution of ester 6-2 (1.0 g, 2.65 mmol) in 20 mL of DCM at 0° C. was treated with 4 mL of CF$_3$COOH. After stirring for 4 hours at RT, the solution was concentrated to an oil. The residue was azeotroped with toluene (6×20 mL) to afford acid 6-3 as a tan solid.

$^1$H NMR (CD$_3$OD) δ 6.11 (s, 1H), 4.83 (s, 2H), 4.07 (t, J=5.04 Hz, 1H), 3.06(s, 3H), 2.33(s, 3H), 1.75 (m, 1H), 1.61 (m, 1H), 0.61 (m, 1H), 0.37 (m, 2H), 0.022 (m, 2H).

HPLC $R_f$=0.4

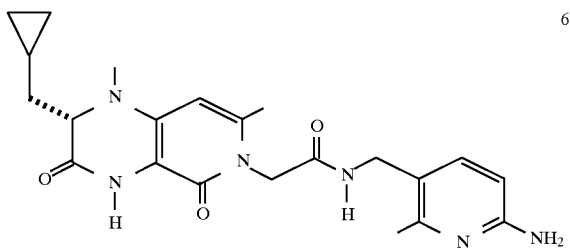

6-4

To a solution of acid 6-3 (500 mg, 1.56 mmol) and 2-BOC-amino-5-aminomethyl-6-methylpyridine (370 mg, 1.56 mmol) in 10 mL of DMF was added HOBT (210 mg, 1.56 mmol), EDC (300 mg, 1.56 mmol), and 0.54 ml of DIPEA. The resulting solution was stirred overnight and concentrated. The residue was redissolved in EtOAc and washed with 5% $Na_2CO_3$, water, and brine. The organic phase was dried ($MgSO_4$) and concentrated to a solid. The solid was dissolved in EtOAc at 0° C. and subjected to HCl(g) for 10 min then stirred for 2 hours. The solution was concentrated to a solid and purified by column chromatography (8% MeOH/$CHCl_3$ (sat'd w/$NH_3$) to afford final product 6-4 as a light yellow solid.

$^1$H NMR ($CD_3OD$) δ 7.36 (d, J=8.42 Hz, 1H), 6.39 (d, J=8.24 Hz, 1H), 6.09 (s, 1H), 4.75 (m, 2H), 4.27 (s, 2H), 4.06 (t, J=5.12 Hz, 1H), 3.06 (s, 3H), 2.34 (s, 3H), 2.31 (s, 3H), 1.75(m, 1H), 1.61 (m, 1H), 0.61 (m, 1H), 0.38 (m, 2H), 0.030 (m, 2H).

HPLC $R_f$=0.41

EXAMPLE 7

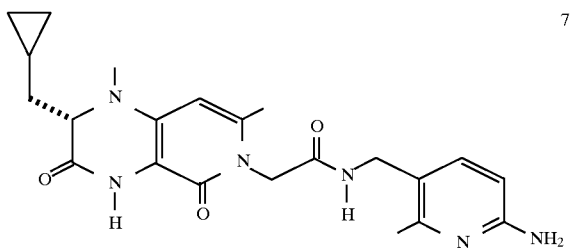

7-1

To a solution of acid 6-3 (150 mg, 0.49 mmol) and 2-BOC-amino-5-aminomethyl pyridine (109 mg, 0.49 mmol) in 3 mL of DMF was added HOBT (66 mg, 0.49 mmol), EDC (93 mg, 0.49 mmol), and 0.17 ml of DIPEA. The resulting solution was stirred overnight and concentrated. The residue was redissolved in EtOAc and washed with 5% $Na_2CO_3$, water, and brine. The organic phase was dried ($MgSO_4$) and concentrated to afford 104 mg (42%) of the penultimate compound as a white solid. This was dissolved in 10 mL of a 95:5 mixture of DCM/MeOH at 0° C. and subjected to HCl(g) for 10 min then stirred for 2.5 hours. The solution was concentrated to a solid and purified by column chromatography (95:5:0.5 DCM/MeOH/$NH_4OH$) to afford 7-1 as a light yellow solid.

$^1$H NMR ($CDCl_3$) δ 9.50 (bs, 1H), 8.00 (bs, 1H), 7.85 (s, 1H), 7.36 (d, J=8.4 Hz, 1H), 6.19 (d, J=8.4 Hz, 1H), 5.77 (s, 1H), 4.80 (d, J=14.8 Hz, 1H), 4.44 (m, 4H), 3.98 (dd, J=4.0 and 14.8 Hz, 1H), 3.80 (t, J=5.5 Hz, 1H), 3.06 (s, 3H), 2.44 (s, 3H), 1.75 (m, 2H), 1.61 (m, 2H), 0.85 (m, 1H), 0.60 (m, 1H), 0.40 (m, 2H).

HPLC $R_f$=0.46

Anal. Calc'd for $C_{21}H_{26}N_6O_3 \cdot 0.2H_2O \cdot 0.5$ EtOAc: C; 60.29, H; 6.69, N; 18.35. Found: C; 60.26, H; 6.46, N; 18.36.

EXAMPLE 8

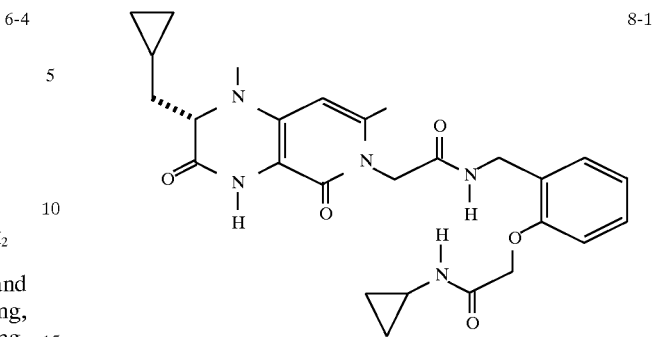

8-1

To a solution of acid 6-3 (150 mg, 0.491 mmol) and N-cyclopropyl(2-aminomethylphenoxy)acetamide (108 mg, 0.491 mmol) in 3 mL of DMF was added HOBT (66 mg, 0.491 mmol), EDC (93 mg, 0.491 mmol), and 0.17 ml of DIPEA. The resulting solution was stirred overnight and concentrated. The residue was redissolved in EtOAc and washed with sat'd. $NaHCO_3$, water, and brine. The organic phase was dried ($MgSO_4$), concentrated and purified by column chromatography (1:9 MeOH/EtOAc) to afford compound 8-1 as a white solid.

$^1$H NMR ($CDCl_3$) δ 8.99 (bs, 1H), 7.80 (bs, 1H), 7.77 (bs, 1H), 7.20 M, 2H), 6.90 (t, J=8 Hz, 1H), 6.70 (d, J=8 Hz, 1H), 5.75 (s, 1H), 4.80–4.45 (m, 4H), 3.95 (t, 2H), 3.06 (s, 3H), 2.80 (m, 1H), 2.45 (s, 3H), 1.61 (m, 1H), 0.61 (m, 6H), 0.80 ( m, 6H), 0.41 (m, 3H).

HPLC $R_f$=0.59

Anal. Calc'd for $C_{27}H_{33}N_5O_5 \cdot 0.1$ $CH_2Cl_2$: C; 63.06, H; 6.48, N; 13.57. Found: C; 63.02, H; 6.21, N; 13.47.

EXAMPLE 9

Tablet Preparation

Tablets containing 100.0, 200.0, and 300.0 mg, respectively, of

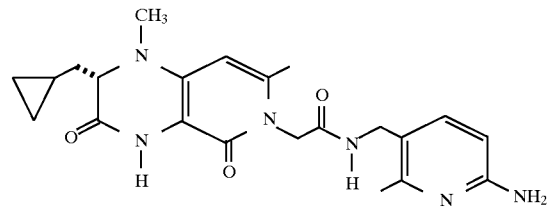

active compound are prepared as illustrated below:

| Ingredient | Amount-mg | | |
|---|---|---|---|
| Active compound | 100.0 | 200.0 | 300.0 |
| Microcrystalline cellulose | 160.0 | 150.0 | 200.0 |
| Modified food corn starch | 20.0 | 15.0 | 10.0 |
| Magnesium stearate | 1.5 | 1.0 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 100.0, 200.0, and 300.0 mg, respectively, of active ingredient per tablet.

EXAMPLE 10

An intravenous dosage form of the above-indicated active compound is prepared as follows:

| | |
|---|---|
| Active compound | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed is:

1. A compound having the following structure:

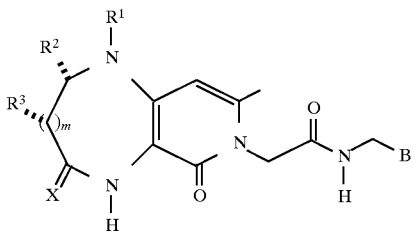

wherein
m is 0;
X is O or $H_2$;
$R^1$, $R^2$ and $R^3$ are independently selected from the group consisting of
hydrogen,
$C_{1-6}$ alkyl-,
$C_{2-6}$ alkenyl,
$C_{2-6}$ alkynyl,
$C_{3-8}$ cycloalkyl-,
$C_{3-8}$cycloalkyl $C_{1-6}$alkyl-,
aryl,
aryl $C_{1-6}$ alkyl-,
wherein aryl is phenyl either unsubstituted or substituted with —OH, —$NH_2$, $C_{1-6}$alkyl, $C_{3-8}$cycloalkyl, or halogen; and
B is

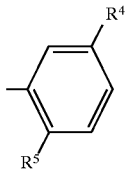

wherein $R^4$ and $R^5$ are independently selected from the group consisting of
hydrogen,
$C_{1-4}$ alkyl,
$C_{2-4}$ alkenyl,
$C_{2-4}$ alkynyl,
$C_{1-4}$ alkoxy,
halogen,
—COOH,
—OH,
—$COOR^7$, where $R^7$ is $C_{1-4}$alkyl,
—$CONR^7$, where $R^7$ and $R^9$ are independently hydrogen or $C_{1-4}$alkyl,
—$OCH_2CO_2H$,
—$OCH_2CO_2CH_3$,
—$OCH_2CO_2(CH_2)_{1-3}CH_3$,
—$O(CH_2)_{1-3}C(O)NR^{10}R^{11}$, wherein $R^{10}$ and $R^{11}$ are independently hydrogen, $C_{1-4}$alkyl, $C_{3-7}$ cycloalkyl, or —$CH_2CF_3$,
—$(CH_2)_{1-4}OH$,
—$NHC(O)CH_3$,
—$NHC(O)CF_3$,
—$NHSO_2CH_3$,
—$SO_2NH_2$; or B is

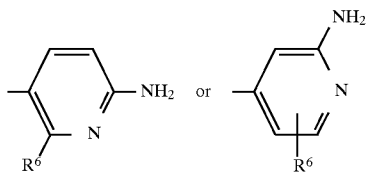

wherein $R^6$ is
hydrogen,
$C_{1-6}$ alkyl-,
$C_{2-6}$ alkenyl-,
$C_{2-6}$ alkynyl,
$C_{3-8}$ cycloalkyl-,
aryl,
aryl $C_{1-6}$alkyl-,
wherein aryl is phenyl either unsubstituted or substituted with —OH, —$NH_2$, $C_{1-6}$alkyl, $C_{3-8}$ cycloalkyl, or halogen,
or a pharmaceutically acceptable salt thereof.

2. The compound of claim 1 having the formula:

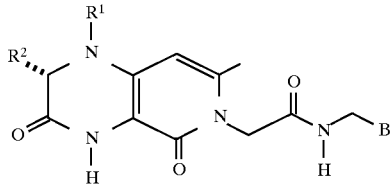

wherein
$R^1$ and $R^2$ are independently selected from the group consisting of:
hydrogen,
$C_{1-6}$alkyl,
$C_{3-8}$cycloalkyl$C_{1-6}$alkyl-,
aryl $C_{1-6}$alkyl-,
wherein aryl is phenyl, and
B is

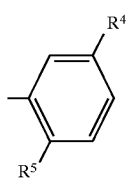

wherein $R^4$ and $R^5$ are independently selected from the group consisting of
hydrogen,
halogen, —OCH₂C(O)NHR¹¹
or B is

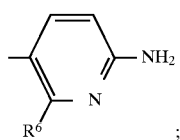
;

where R⁶ is hydrogen or —CH₃,
or a pharmaceutically acceptable salt thereof.

3. The compound of claim 2 having the formula:

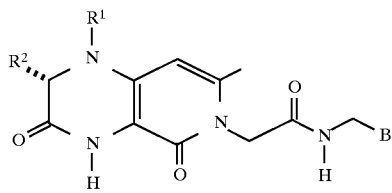

wherein

R¹ and R² are independently selected from the group consisting of:

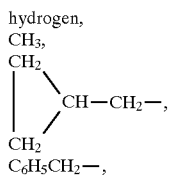

and

B is

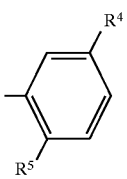

wherein R⁴ and R⁵ are independently selected from the group consisting of

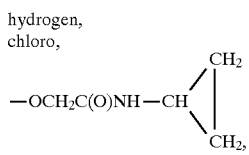

or B is

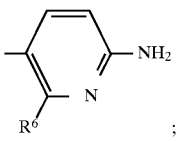
;

where R⁶ is hydrogen or —CH₃, or a pharmaceutically acceptable salt thereof.

4. The compound of claim 3 selected from the group consisting of:

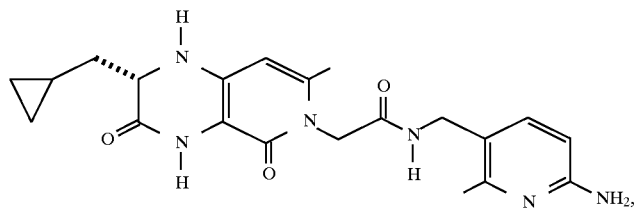

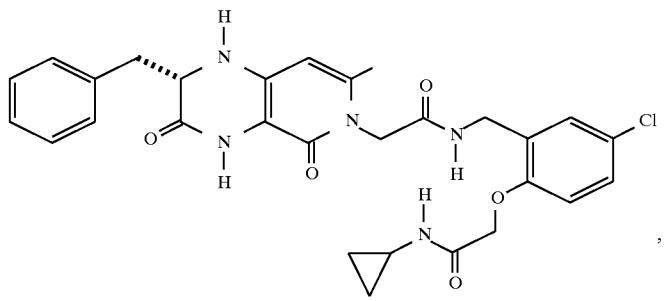

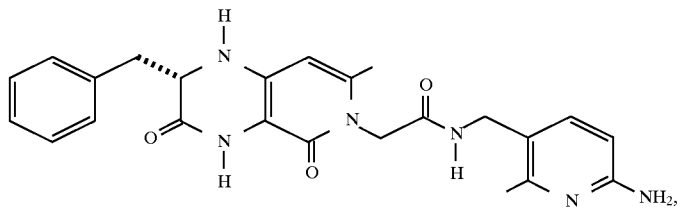

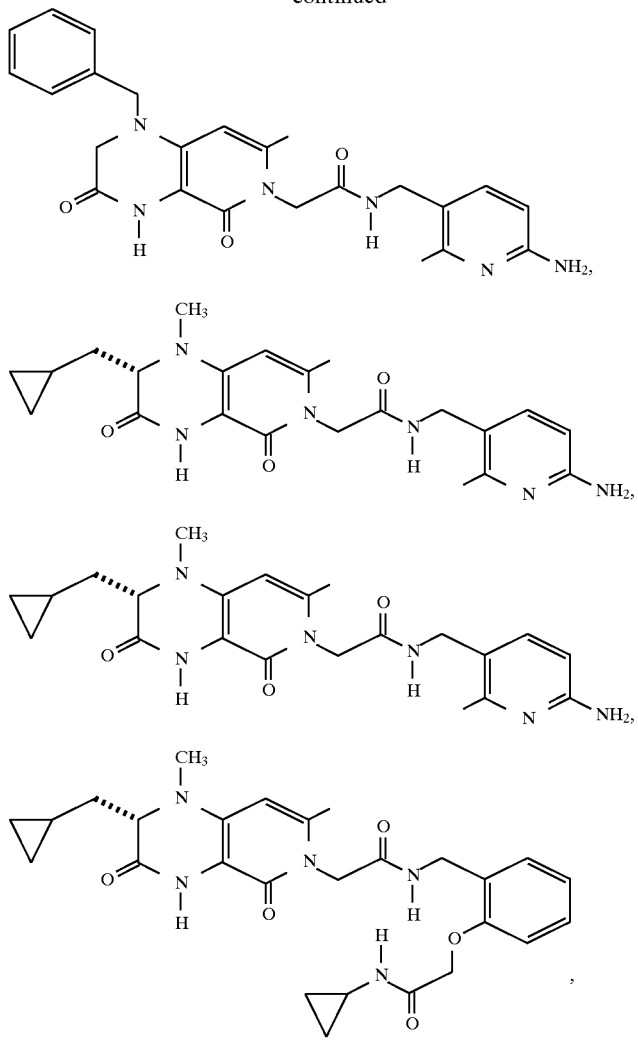
or a pharmaceutically acceptable salt thereof.
5. A composition for inhibiting thrombin in blood comprising a therapeutically effective amount of compound of claim 1 and a pharmaceutically acceptable carrier.
6. A method for inhibiting thrombin in blood in a patient comprising administering to the patient a composition of claim 5.
* * * * *